United States Patent [19]

Geisen et al.

[11] Patent Number: 5,138,058
[45] Date of Patent: Aug. 11, 1992

[54] PIPERAZINE SUBSTITUTED PYRIMIDINE DERIVATIVES AND PHYSIOLOGICALLY TOLERATED SALTS THEREOF

[75] Inventors: Karl Geisen, Frankfurt am Main; Hans-Jochen Lang, Hofheim am Taunus; Hildegard Nimmesgern, Frankfurt am Main; Klaus Weidmann, Kronberg/Taunus, all of Fed. Rep. of Germany

[73] Assignee: Hoechst Aktiengesellschaft, Frankfurt am Main, Fed. Rep. of Germany

[21] Appl. No.: 482,053

[22] Filed: Feb. 20, 1990

[30] Foreign Application Priority Data

Feb. 22, 1989 [DE] Fed. Rep. of Germany ....... 3905364

[51] Int. Cl.$^5$ ............................................ C07D 403/04
[52] U.S. Cl. .................................... 544/295; 544/326; 544/327
[58] Field of Search ........................ 544/326, 327, 295

[56] References Cited

U.S. PATENT DOCUMENTS

| | | | |
|---|---|---|---|
| 3,624,084 | 11/1971 | Mathieu | 544/326 |
| 3,707,560 | 12/1972 | De Angelis et al. | 544/326 |
| 3,859,288 | 1/1975 | De Angelis et al. | 544/326 |
| 3,932,408 | 1/1976 | Eck et al. | 544/326 |
| 4,014,677 | 3/1977 | Fischer | 544/326 |
| 4,314,818 | 2/1982 | Courtin | 544/326 |
| 4,323,681 | 4/1982 | Wolf et al. | 544/326 |
| 4,885,296 | 12/1989 | Mahoury et al. | 544/295 |
| 4,975,530 | 12/1990 | Tzikas et al. | 544/295 |

FOREIGN PATENT DOCUMENTS

| | | |
|---|---|---|
| 1695975 | 5/1971 | Fed. Rep. of Germany . |
| 2149249 | 4/1972 | Fed. Rep. of Germany . |
| 2152742 | 4/1972 | Fed. Rep. of Germany . |
| 2963052 | 7/1974 | Fed. Rep. of Germany . |
| 2520381 | 11/1975 | Fed. Rep. of Germany . |
| 2433176 | 1/1976 | Fed. Rep. of Germany . |
| 959699 | 6/1964 | United Kingdom . |
| 1329369 | 9/1973 | United Kingdom . |
| 1342828 | 1/1974 | United Kingdom ................ 544/295 |
| 2198132 | 6/1988 | United Kingdom . |

OTHER PUBLICATIONS

Journal of the Chemical Society, Chemical Communications No. 24, 1976, pp. 1060, 1061, J. H. Forsberg et al.
Journal of Organic Chemistry, vol. 52, 1987, pp. 1017–1021, J. H. Forsberg et al.

*Primary Examiner*—C. Warren Ivy
*Assistant Examiner*—Raymond Covington
*Attorney, Agent, or Firm*—Finnegan, Henderson, Farabow, Garrett and Dunner

[57] ABSTRACT

Pyrimidine derivatives of the formula I

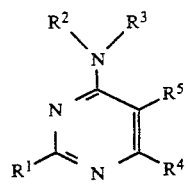

in which $R^1$, $R^2$, $R^3$, $R^4$ and $R^5$ have the indicated meanings, the salts thereof, and a process for the preparation thereof are described. Because of their sorbitol-accumulating activity, they are suitable as a tool in a pharmacological screening model for aldose reductase inhibitors.

6 Claims, No Drawings

PIPERAZINE SUBSTITUTED PYRIMIDINE DERIVATIVES AND PHYSIOLOGICALLY TOLERATED SALTS THEREOF

DESCRIPTION

Elevated intracellular sorbitol concentrations are regarded as a cause of delayed damage due to diabetes, such as, for example, retinopathy, neuropathy and nephropathy. The formation of sorbitol by the enzyme aldose reductase is increased when the blood glucose is elevated. Sorbitol accumulation can be prevented by aldose reductase inhibitors.

Screening for aldose reductase inhibitors (ARI) is carried out on rats with diabetes induced by streptozotocin. The animals are employed in the ARI screening 1 to 2 weeks after the induction of diabetes with 60 mg of streptozotocin sulfate per kg of rat. The measure used for the activity of aldose reductase inhibitors is the lowering of the elevated sorbitol content in erythrocytes, in nerves and in the lens 5-6 h after treatment with the ARIs to be investigated.

Streptozotocin is a carcinogen. Administration of streptozotocin and housing of the animals after administration (2-3 days) must therefore take place under biohazard conditions. The urine excreted in the first 2 days following streptozotocin administration must be disposed of in a special way, and the contaminated boxes must be specially cleaned. However, streptozotocin is not only carcinogenic and toxic for beta cells, it also causes liver and kidney damage. This is why the animals are not employed in the ARI screening until 10-14 days after administration.

It has now been found, surprisingly, that pyrimidine derivatives of the formula I

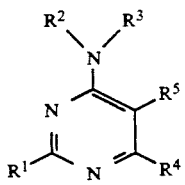

and the pharmacologically tolerated salts thereof cause an increase in intracellular sorbitol, without having an acute and chronic effect on blood glucose, when administered orally or parenterally. The increase in sorbitol induced by the pyrimidine derivatives of the formula I is prevented by simultaneous treatment with aldose reductase inhibitors. The sorbitol-accumulating pyrimidine derivatives are therefore suitable for a new, simplified, less cost-intensive and time-consuming acute screening for aldose reductase inhibitors in normal, non-diabetic rats.

It is also possible to show, by induction of functional and morphological alterations of the nature of delayed damage due to diabetes in animals chronically treated with pyrimidine derivatives of the formula I, for example by administration in the drinking water, that the intracellular sorbitol accumulation actually is the direct cause of the delayed damage due to diabetes.

Parameters of delayed damage due to diabetes are: the nerve conduction velocity, dilatation of pupils, retinal capillary aneurysms, thickness of the basement membrane of the capillaries.

The present invention therefore relates to pyrimidine derivatives of the formula I

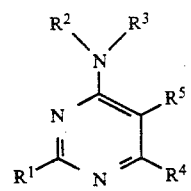

in which $R^1$, $R^4$ and $R^5$ are identical or different and denote hydrogen, halogen, cyano, nitro, trifluoromethyl, $(C_1-C_6)$-alkyl, $(C_1-C_6)$-hydroxyalkyl, $(C_1C_6)$-alkoxy, $(C_6-C_{12})$-aryl or amino, $R^2$, $R^3$ are identical or different and are hydrogen, $(C_1-C_6)$-alkyl, $(C_6-C_{12})$-aryl or $(C_6-C_{12})$-aralkyl with 1-4 alkyl carbon atoms, or $R^2$ and $R^3$ form, together with the nitrogen to which they are bonded, the azetidino, pyrrolidino, piperidino, piperazino, or morpholino group, or an azetidino, pyrrolidino, piperidino, piperazino or morpholino group which is substituted by identical or different groups $R^6$ and $R^7$, where $R^6$, $R^7$ denote $(C_6-C_6)$-alkyl, sulfamoyl, N-$(C_1-C_4)$-alkylsulfamoyl, N,N-$(C_1-C_4)$-dialkylsulfamoyl, $(C_1-C_6)$-alkoxycarbonyl, N,N-$(C_1-C_4)$-dialkylcarbamoyl, N-$(C_1-C_4)$-alkylcarbamoyl, N-$(C_6-C_{12})$-arylcarbamoyl, or $(C_6-C_{12})$-arylcarbamoyl which is substituted in the aryl radical by $(C_1-C_4)$-alkyl, $(C_1-C_4)$-alkoxy, halogen, $NO_2$, $NH_2$, CN or $CF_3$, or carbamoyl, $(C_1-C_6)$-alkylcarbonyl, or $(C_6-C_{12})$-arylcarbonyl, or $(C_6-C_{12})$-arylcarbonyl which is substituted in the aryl radical by $(C_1-C_4)$-alkyl, $(C_1-C_4)$-alkoxy, halogen, $NO_2$, $NH_2$, CN or $CF_3$, or $(C_1-C_6)$-alkylsulfonyl,$(C_1-C_6)$-alkylsulfinyl,$(C_6-C_{12})$-arylsulfonyl, or $(C_6-C_{12})$-arylsulfonyl which is substituted in the aryl radical by $(C_1-C_4)$-alkyl, $(C_1-C_4)$-alkoxy, halogen, $NO_2$, $NH_2$, CN or $CF_3$, or heteroarylcarbonyl or heteroarylsulfonyl, or one of the substituents $R^6$, $R^7$ is hydrogen, as well as the physiologically tolerated salts thereof.

In the definitions hereinbefore and hereinafter, alkyl and alkoxy (including in derived radicals) stand for straight-chain or branched radicals, halogen stands for fluorine, chlorine, bromine and iodine, in particular for chlorine.

Heteroaryl is defined as an unsubstituted heteroaryl radical which has as heteroatom(s) an oxygen atom or 1 to 3 nitrogen atoms. $(C_6-C_{12})$-aryl is, for example, phenyl, naphthyl or biphenylyl.

Preferred pyrimidine derivatives of the formula I are those in which $R^1$, $R^4$ and $R^5$ are identical or different and are hydrogen or $(C_1-C_6)$-alkyl, and $R^2$, $R^3$ form, together with the nitrogen to are bonded, a piperazine ring which is optionally substituted by identical or different groups $R^6$ and $R^7$, where $R^6$, $R^7$ are $(C_1-C_6)$-alkyl, sulfamoyl, N-$(C_1-C_4)$-alkylsulfamoyl, N,N-$(C_1-C_4)$-dialkylsulfamoyl, $(C_1-C_6)$-alkoxycarbonyl, N,N-$(C_1-C_4)$-dialkylcarbamoyl, N-$(C_1C_4)$-alkylcarbamoyl, carbamoyl, $(C_1-C_6)$-alkylcarbonyl, $(C_6-C_{12})$-arylcarbonyl, or $(C_6C_{12})$-arylcarbonyl which is substituted in the aryl radical by $(C_1-C_4)$-alkyl, $(C_1-C_4)$-alkoxy, halogen, $NO_2$, $NH_2$, CN or $CF_3$, or $(C_1-C_6)$-alkylsulfonyl, $(C_1-C_6)$-alkylsulfinyl, $(C_6-C_{12})$-arylsulfonyl, or $(C_6-C_{12})$-arylsulfonyl which is substituted in the aryl radical by $(C_1-C_4)$-alkyl, $(C_1-C_4)$- alkoxy, halogen, $NO_2$, $NH_2$, CN or $CF_3$, or heteroarylcarbonyl or heteroarylsulfonyl, or one of the substituents $R^6$, $R^7$ is hydrogen, as well as the physiologically tolerated salts thereof.

Particularly preferred pyrimidine derivatives of the formula I are those in which $R^1$, $R^4$ and $R^5$ are identical or different and are hydrogen or $(C_1-C_4)$-alkyl, and $R^2$, $R^3$ form, together with the nitrogen to which they are bonded, a piperazine ring which optionally carries in position 4 another substituent $R^6$, where $R^6$ is sulfamoyl, $N-(C_1-C_4)$-alkylsulfamoyl, $N,N-(C_1-C_4)$-dialkylsulfamoyl, carbamoyl, $N-(C_1-C_4)$alkylcarbamoyl, $N,N-(C_1C_4)$-dialkylcarbamoyl, $(C_1-C_6)$-alkylcarbonyl, $(C_6-C_{12})$-arylcarbonyl, or $(C_6-C_{12})$-arylcarbonyl which is substituted in the aryl radical by $(C_1-C_4)$-alkyl, $(C_1-C_4)$-alkoxy, halogen, $NO_2$, $NH_2$, CN or $CF_3$, or pyridinecarbonyl, as well as the physiologically tolerated salts thereof.

Very particularly preferred pyrimidine derivatives of the formula I are those in which $R^1$ is hydrogen or $(C_1-C_2)$-alkyl, in particular methyl, $R^4$ is hydrogen or $(C_{10}-C_2)$-alkyl, in particular hydrogen, $R^5$ is hydrogen, $R^2$, $R^3$ form, together with the nitrogen to which they are bonded, a piperazine ring which optionally carries in position 4 another substituent $R^6$, where $R^6$ represents $N-(C_1-C_3)$-alkylsulfamoyl, $N,N-(C_1-C_2)$-dialkylsulfamoyl, $N-(C_1-C_2)$-alkylcarbomoyl, $N,N-(C_1-C_2)$-dialkylcarbamoyl, $(C_1-C_2)$-alkylcarbonyl, phenylcarbonyl which is optionally substituted in the phenyl radical by $(C_1-C_2)$-alkyl, chlorine or $NO_2$, or pyridinecarbonyl, in particular N,N-dimethylsulfamoyl, phenylcarbonyl or pyridinecarbonyl, as well as the physiologically tolerated salts thereof.

The invention furthermore relates to a process for the preparation of compounds of the formula I, which comprises, in a manner known per se, a) reacting a compound of the formula II

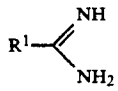

in which $R^1$ has the meanings indicated for formula I or the acid addition salt thereof, with a compound of the formula III

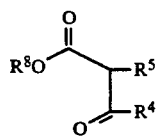

in which $R^4$ and $R^5$ have the meanings indicated for formula I, and $R^8$ is methyl or ethyl, or with a base salt thereof, to give a compound of the formula IV

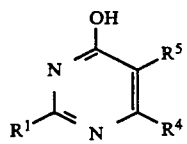

in which $R^1$, $R^4$ and $R^5$ have the meanings indicated for formula I, b) reacting a resulting compound IV with an inorganic acid chloride such as, for example, with phosphorus oxychloride, to give a pyrimidine derivative of the formula V

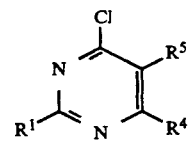

in which the radicals $R^1$, $R^4$ and $R^5$ have the meanings indicated for formula I, c) reacting a resulting compound of the formula V with an amine of the formula VI

in which $R^2$ and $R^3$ have the meanings indicated for formula I, to give a compound of the formula I, and d) where appropriate converting a resulting compound of the formula I in which one or both of the substituents $R^2/R^3$ is hydrogen into a compound in which $R^2/R^3$ have the meanings indicated for formula I, with the exception of hydrogen, e) where appropriate introducing the radical(s) $R^6/R^7$ into a resulting compound of the formula I in which $R^2$ and $R^3$ form, together with the nitrogen atom carrying them, the azetidino, pyrrolidino, piperidino, piperazino or morpholino radical, and f) where appropriate converting a resulting compound of the formula I into a physiologically tolerated salt.

The process according to the invention is carried out in analogy to the processes described in the literature (cf. for example, D. J. Brown, The Chemistry of Heterocyclic Compounds, The Pyrimidines Suppl. I (1970), Suppl. II (1985), Wiley-Interscience New York and literature cited therein).

Reaction of compounds of the formula V with ammonia (formula VI, $R^2=R^3=H$) or primary amines (formula VI, $R^2=H$, $R_3 \neq H$) results in compounds of the formula I with $R^2=R^3=H$ or $R^2=H$, $R^3 \neq H$, and their (remaining) hydrogen atoms can optionally be replaced by reaction with compounds $Z-R^2/Z-R^3$ in which Z denotes chlorine, bromine or iodine, and $R^2$, $R^3$ have the meanings indicated for formula I, with the exception of hydrogen.

Reaction of compounds of the formula V with amines of the formula VI in which $R^2$, $R^3$ form, together with the nitrogen to which they are bonded, a ring system results in compounds of the formula I in which the ring system either already carries the substituents $R^6$, $R^7$, as has been defined above, or is unsubstituted. If this ring system, for example as in the piperazine, still carries acidic hydrogen atoms, the latter can optionally be replaced by reaction with compounds $Z-R^6/Z-R^7$, in which Z denotes chlorine, bromine or iodine, and $R^6/R^7$ have the meanings indicated for formula I.

Compounds of the formula I can be converted into their physiologically tolerated salts by reaction with acids.

The compounds according to the invention provoke, owing to an intracellular polyol accumulation, without a diabetic metabolic status functional symtoms of the nature of diabetic neuropathy.

Pharmacological investigation

Administered orally in doses of 5-50 mg/kg of rat, the compounds according to the present invention caused, within 4 to 5 hours, a dose-dependent increase in the sorbitol concentration in the sciatic nerve and in the erythrocytes of normal rats and rats with diabetes induced by streptozotocin.

4-5 Hours after oral administration of 25 mg/kg of rat of the compound of Example 1d, the sorbitol concentration reached in the said tissues in normal rats corresponds to that shown after 8 days by rats with diabetes induced by streptozotocin. The increase in sorbitol is prevented dose-dependently by simultaneous oral treatment with the ARI spiro-2,7-difluoro-9H-fluorene-9,4'-imidazolidine-2,5-dione (=HOE 843).

Because of the ability to bring about sorbitol accumulation, the compounds according to the invention are particularly suitable as a tool in a pharmacological model for testing aldose reductase inhibitors. The invention therefore also relates to this use of the pyrimidine derivatives of the formula I and of the pharmacologically tolerated salts thereof.

Apart from the compounds listed in the Examples, the compounds of the general formula I, and the salts thereof, which are collected in the following Table can be obtained.

Abbreviations used: methyl (Me), ethyl (Et), propyl (Pr), butyl (Bu), hexyl (Hex), acetyl (Ac), phenyl (Ph), iso (i) and cyclo (c).

TABLE (Formula I with $R^2R^3$ = piperazinyl-$R^6$).

| $R^1$ | $R^4$ | $R^5$ | $R^6$ |
|---|---|---|---|
| H | H | H | H |
| H | H | H | —SO$_2$—C$_6$H$_4$—CH$_3$ |
| H | H | H | —SO$_2$—C$_6$H$_4$—NO$_2$ |
| H | H | H | —SO$_2$—CH$_3$ |
| H | H | H | —SO$_2$—N(Me)$_2$ |
| H | H | H | —SO$_2$—NHCH$_3$ |
| H | H | H | —CO—C$_6$H$_5$ |
| H | H | H | —CO—CH$_3$ |
| H | H | H | —CO—C$_6$H$_4$—CH$_3$ |
| H | H | H | —CO—C$_6$H$_4$—NO$_2$ |
| H | H | H | —CO—C$_6$H$_4$—Cl |
| H | H | H | —SO$_2$—N(Et)$_2$ |
| H | H | H | —SO$_2$—N(iPr)$_2$ |
| H | H | H | —CO—C$_6$H$_3$(Cl)(CH$_3$) |
| H | H | H | —CO—C$_6$H$_3$(Cl)(NO$_2$) |
| H | H | H | —CO—NHEt |
| CH$_3$ | H | H | H |
| CH$_3$ | H | H | —SO$_2$—NHCH$_3$ |
| CH$_3$ | H | H | —CO—C$_6$H$_4$—CH$_3$ |
| CH$_3$ | H | H | —CO—C$_6$H$_4$—NO$_2$ |
| CH$_3$ | H | H | —CO—C$_6$H$_4$—Cl |
| CH$_3$ | H | H | —CO—C$_6$H$_3$(Cl)(CH$_3$) |
| CH$_3$ | H | H | —CO—C$_6$H$_3$(Cl)(NO$_2$) |

TABLE-continued (Formula I with R²R³ = —N‿N—R⁶, piperazine attached to pyrimidine with R¹, R⁴, R⁵ substituents)

| R¹ | R⁴ | R⁵ | R⁶ |
|---|---|---|---|
| CH₃ | H | H | —SO₂—N(Et)₂ |
| CH₃ | H | H | —CO—CH₃ |
| CH₃ | H | H | —CO—N(Me)₂ |
| CH₃ | H | H | —CO—NH—C₆H₅ |
| CH₃ | H | H | —CO—NH—C₆H₄—NO₂ |
| CH₃ | H | H | —CO—C₆H₄—OCH₃ |
| CH₃ | H | H | —CO—(2-pyridyl) |
| CH₃ | H | H | —CO—(4-pyridyl) |
| Et | H | H | H |
| Et | H | H | —SO₂—C₆H₄—CH₃ |
| Et | H | H | —SO₂—C₆H₄—NO₂ |
| Et | H | H | —SO₂—CH₃ |
| Et | H | H | —SO₂—NH(CH₃) |
| Et | H | H | —SO₂—N(CH₃)₂ |
| Et | H | H | —SO₂—NEt₂ |
| Et | H | H | —SO₂—N(iPr)₂ |
| Et | H | H | —SO₂—Et |
| Et | H | H | —COCH₃ |
| Et | H | H | —CO—C₆H₄—OCH₃ |
| Et | H | H | —CO—C₆H₄—NO₂ |
| Et | H | H | —CO—C₆H₄—Cl |
| Et | H | H | —CO—C₆H₄—CH₃ |
| Et | H | H | —CO—C₆H₃(Cl)(CH₃) |
| Et | H | H | —CO—C₆H₃(Cl)(CH₃) |
| Et | H | H | —CO—C₆H₃(Cl)(NO₂) |
| Et | H | H | —CO—C₆H₃(Cl)(Cl) |
| Et | H | H | —CO—(2-pyridyl) |
| Et | H | H | —CO—(3-pyridyl) |
| Et | H | H | —CO—(4-pyridyl) |

The Examples which follow serve to illustrate the invention without intending to confine it thereto:

EXAMPLE 1

2-Methyl-4-(4-N,N-dimethylsulfamoyl-piperazino)-pyrimidine and the corresponding hydrochloride a) 4-Hydroxy-2-methyl-pyrimidine A mixture of 555 g of ethyl formate and 440 g of ethyl acetate was added dropwise at room temperature to a stirred suspension of 240 g of sodium hydride (55% suspension) in 5 l of toluene until the evolution of hydrogen ceased. The mixture was then stirred for 1 h, and the precipitate was filtered off with suction and washed with ether. 650 g of the sodium salt of ethyl formylacetate were obtained and were dissolved in 4 l of water and reacted with 475 g of acetamidine hydrochloride. The reaction solution was left to stand at room temperature for 2 days, and then the water was removed by distillation in vacuo and the residue was chromatographed on silica gel. 240 g of 4-hydroxy-2-methyl-pyrimidine were obtained (Melting point: 214° C.)

b) 4-Chloro-2-methyl-pyrimidine 50 ml of phosphorus oxychloride were added to 11 g of 4-hydroxy-2-methyl-pyrimidine, and the mixture was slowly heated to 80° C. Once the solid had completely dissolved, excess phosphorus oxychloride was removed by distillation in vacuo and the residue was poured onto ice. The aqueous phase was extracted several times with dichloromethane, and the organic phases were dried over sodium sulfate, filtered and concentrated. 8 g of 4-chloro-2-methyl-pyrimidine were obtained. (Melting point: 59° C.)

c) 2-Methyl-4-piperazino-pyrimidine 13 g of 4-chloro-2-methyl-pyrimidine were dissolved in 200 ml of tetrahydrofuran, and 17.5 g of piperazine were added. The reaction mixture was refluxed for 24 h. The precipitated piperazine hydrochloride was filtered off with suction and washed with tetrahydrofuran. Concentration of the solution in vacuo resulted in 19 g of 2-methyl-4-piperazino-pyrimidine, which was reacted without further purification.

d) 2-Methyl-4-(4-N,N-dimethylsulfamoyl-piperazino)pyrimidine 5 g of 2-methyl-4-piperazino-pyrimidine were dissolved in 80 ml of pyridine and, at room temperature, 4.7 g of N,N-dimethylamidosulfonyl chloride were added. The reaction solution was heated at 50° C. for 5 h. Once the starting compound had completely reacted, the reaction mixture was cooled to room temperature, and then diethyl ether was added. The crystals which separated out were filtered off with suction. Purification by column chromatography resulted in 2.6 g of 2-methyl-4-(4-N,N-dimethylsulfamoylpiperazino)-pyrimidine. (Melting point: 114° C.)

e) 2-Methyl-4-(N,N-dimethylsulfamoyl-piperazino)-pyrimidine hydrochloride 1 g of 2-methyl-4-(N,N-dimethylsulfamoyl-piperazino)pyrimidine was dissolved in 5 ml of methanol and, at room temperature, 10 ml of methanolic hydrochloric acid were added, while stirring. After 15 minutes, the solvent was removed by distillation in vacuo, and acetone was added to the residue. 1 g of the hydrochloride was isolated as white crystals. (Melting point: 238° C., decomposition)

EXAMPLE 2

2-Methyl-4-(4-benzoyl-piperazino)-pyrimidine 1 g of 2-methyl-4-piperazino-pyrimidine was dissolved in 50 ml of acetone, and 2 g of potassium carbonate and 0.8 g of benzoyl chloride were added. The suspension was refluxed for 6 h until starting compound was no longer detectable. After filtration, the filtrate was concentrated in vacuo, and the residue was recrystallized from dichloromethane/petroleum ether. 0.5 g of 2-methyl-4-(4-benzoyl-piperazino)-pyrimidine was obtained. (Melting point: 147° C.)

The following compounds were prepared in an analogous manner.

EXAMPLE 3

2-Methyl-4-(4-ethylcarbamoyl-piperazino)-pyrimidine (Melting point: 138° C.)

EXAMPLE 4

2-Methyl-4-(4-methanesulfonylpiperazino)-pyrimidine (Melting point: 241° C.) (decomposition)

EXAMPLE 5

2-Methyl-4-[4-(4-nitrobenzenesulfonyl)-piperazino]-pyrimidine (Melting point: 166° C.)

EXAMPLE 6

2-Methyl-4-[4-( p-toluenesulfonyl)-piperazino]-pyrimidine (Melting point: 142° C.)

EXAMPLE 7

2-Methyl-4-(4-nicotinoyl-piperazino)-pyrimidine (Melting point: 118° C.)

EXAMPLE 8

6-Methyl-4-(4-benzoyl-piperazino)-pyrimidine (Melting point: 132° C.)

EXAMPLE 9

6-Methyl-4-[4-(p-toluenesulfonyl)-piperazino]-pyrimidine (Melting point: 221° C.)

EXAMPLE 10

6-Methyl-4-(4-nicotinoyl-piperazino)-pyrimidine (Melting point: 78° C.)

EXAMPLE 11

6-Methyl-4-(4-N,N-dimethylsulfamoylpiperazino)-pyrimidine (Melting point: 107° C.)

EXAMPLE 12

6-Methyl-4-(4-methanesulfonylpiperazino)-pyrimidine (Melting point: 198° C.)

We claim:

1. A pyrimidine derivative of the formula I

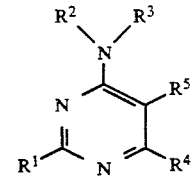

in which

R$^1$, R$^4$ and R$^5$ are identical or different and are hydrogen, halogen, cyano, nitro, trifluoromethyl, ($C_1$-$C_6$)-alkyl, ($C_1$-$C_6$)-hydroxyalkyl, ($C_1$-$C_6$)-alkoxy, ($C_6$-$C_{12}$)-aryl or amino, R$^2$, R$^3$ form, together with the nitrogen to which they are bonded, the piperazino group which is substituted by sulfamoyl, N-($C_1$-$C_4$)-alkylsulfomoyl, N,N-($C_1$-$C_4$)-dialkylsulfamoyl, N,N-($C_1$-$C_4$)-dialkylcarbomoyl, N-($C_1$-$C_4$)-alkylcarbomoyl, N-($C_6$-$C_{12}$)-arylcarbomoyl, or ($C_6$-$C_{12}$)-arylcarbomoyl which is substituted in the aryl radical by ($C_1$–$C_4$)-alkyl, ($C_1$–$C_4$)-alkoxy, halogen, $NO_2$, $NH_2$, CN or $CF_3$, or the physiologically tolerated salts thereof.

2. A pyrimidine derivative as claimed in claim 1, or the physiologically tolerated salts thereof, wherein in formula I at least one of the substituents has the following meaning:

$R^1$, $R^4$ and $R^5$ are identical or different, and are hydrogen or ($C_1$–$C_6$)-alkyl, and $R^2$, $R^3$ form, together with the nitrogen to which they are bonded, a piperazine ring which is substituted by sulfamoyl, N-($C_1$–$C_4$)-alkylsulfamoyl, N,N-($C_1$–$C_4$)-dialkylsulfamoyl, N,N-($C_1$–$C_4$)-dialkylcarbomoyl or N-($C_1$–$C_4$)-alkylcarbomoyl.

3. A pyrimidine derivative as claimed in claim 1, or the physiologically tolerated salts thereof, wherein in formula I at least one of the substituents has the following meaning:

$R^1$, $R^4$ and $R^5$ are identical or different and are hydrogen or ($C_1$–$C_4$)-alkyl, and $R^2$, $R^3$ together with the nitrogen to which they are bonded, a piperazine ring which carries in position 4 another substituent which is sulfamoyl, N-($C_1$–$C_4$)-alkylsulfamoyl, N,N-($C_1$–$C_4$)-dialkylsulfamoyl, N-($C_1$–$C_4$)-alkylcarbomoyl or N,N-($C_1$–$C_4$)-dialkylcarbomoyl.

4. A pyrimidine derivative as claimed in claim 1, or the physiologically tolerated salts thereof, wherein in formula I at least one of the substituents has the following meaning:

$R^1$ hydrogen or ($C_1$–$C_2$)-alkyl, $R^4$ hydrogen or ($C_1$–$C_2$)-alkyl, $R^5$ hydrogen, $R^2$, $R^3$ form, together with the nitrogen to which they are bonded, a piperazine ring which carries in position 4 another substituent N-($C_1$–$C_3$)-alkylsulfamoyl, N,N-($C_1$–$C_2$)-dialkylsulfamoyl, N-($C_1$–$C_2$)-alkylcarbomoyl or N,N-($C_1$–$C_2$)dialkylcarbomoyl.

5. A pyrimidine derivative as claimed in claim 4, or the physiologically tolerated salts thereof, wherein in formula I, $R^1$ is methyl.

6. A pyrimidine derivative as claimed in claim 4, or the physiologically tolerated salts thereof, wherein in formula I, $R^4$ is hydrogen.

* * * * *

UNITED STATES PATENT AND TRADEMARK OFFICE
CERTIFICATE OF CORRECTION

PATENT NO. : 5,138,058

DATED : August 11, 1992

INVENTOR(S) : Karl Geisen et al.

It is certified that error appears in the above-identified patent and that said Letters Patent is hereby corrected as shown below:

Claim 1, Column 10, Lines 65-68, change "N,N-($C_1$-$C_4$)-dialkylcarbomoyl, N-($C_1$-$C_4$)-alkylcarbomoyl, N-($C_6$-$C_{12}$)-arylcarbomoyl, or ($C_6$-$C_{12}$)-arylcarbomoyl" to -- N,N-($C_1$-$C_4$)-dialkylcarbamoyl, N-($C_1$-$C_4$)-alkylcarbamoyl, N-($C_6$-$C_{12}$)-arylcarbamoyl, or ($C_6$-$C_{12}$)-arylcarbamoyl--.

Claim 2, Column 11, Lines 12-13, change "N,N-($C_1$-$C_4$)-dialkylcarbomoyl or N-($C_1$-$C_4$)-alkylcarbomoyl" to --N,N-($C_1$-$C_4$)-dialkylcarbamoyl or N-($C_1$-$C_4$)-alkylcarbamoyl--.

Claim 3, Column 12, Lines 2-3, change "N-($C_1$-$C_4$)-alkylcarbomoyl or N,N-($C_1$-$C_4$)-dialkylcarbomoyl" to --N-($C_1$-$C_4$)-alkylcarbamoyl or N,N-($C_1$-$C_4$)-dialkylcarbamoyl--.

UNITED STATES PATENT AND TRADEMARK OFFICE
CERTIFICATE OF CORRECTION

PATENT NO. : 5,138,058
DATED : August 11, 1992
INVENTOR(S) : Karl Geisen et al.

It is certified that error appears in the above-indentified patent and that said Letters Patent is hereby corrected as shown below:

Claim 4, Column 12, Line 15, change "alkylcarbomoyl or N,N-$(C_1-C_2)$dialkylcarbomoyl" to --alkylcarbamoyl or N,N-$(C_1-C_2)$-dialkylcarbamoyl--.

Signed and Sealed this

Fourteenth Day of December, 1993

Attest:

BRUCE LEHMAN

*Attesting Officer*  *Commissioner of Patents and Trademarks*